United States Patent [19]

Whittle

[11] Patent Number: 4,792,563

[45] Date of Patent: Dec. 20, 1988

[54] INSECTICIDAL ETHERS

[75] Inventor: Alan J. Whittle, Twyford, United Kingdom

[73] Assignee: Imperial Chemical Industries PLC, London, England

[21] Appl. No.: 105,024

[22] Filed: Oct. 6, 1987

[30] Foreign Application Priority Data

Oct. 16, 1986 [GB] United Kingdom ............... 8624831

[51] Int. Cl.$^4$ .................. C07D 213/62; C07D 213/28; C07D 213/72; C07C 43/02

[52] U.S. Cl. ........................... 514/345; 546/301; 546/302; 546/339; 546/304; 568/637; 568/636; 568/659; 568/661; 564/433; 514/277; 514/352; 514/568; 514/721; 514/717

[58] Field of Search ............... 546/301, 302, 339, 304; 568/637, 636, 659, 661; 564/433; 514/345, 352, 277, 568, 721, 717

[56] References Cited

U.S. PATENT DOCUMENTS

| | | | |
|---|---|---|---|
| 4,073,812 | 2/1978 | Bull et al. | 546/301 |
| 4,397,864 | 8/1983 | Nakatani et al. | 546/301 |
| 4,599,362 | 7/1986 | Nakatani et al. | 546/301 |
| 4,655,824 | 4/1987 | Mengel et al. | 546/302 |
| 4,664,698 | 5/1987 | Tsushima et al. | 546/301 |
| 4,678,811 | 7/1987 | Franke et al. | 546/301 |

Primary Examiner—Alan L. Rotman
Assistant Examiner—Robert C. Whittenbaugh
Attorney, Agent, or Firm—Cushman, Darby & Cushman

[57] ABSTRACT

Insecticidally active compounds of the formula (I):

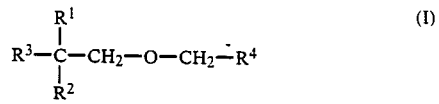

(I)

wherein $R^4$ represents a group selected from those groups represented by $R^5$ in insecticidally active compounds of formula:

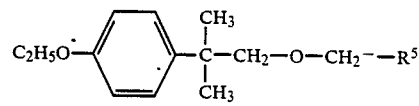

$R^3$ is selected from fluoromethyl and difluoromethyl, and either (a) $R^1$ and $R^2$ represent alkyl of one, two, three or four carbon atoms, or (b) $R^1$ and $R^2$ taken together with the adjacent carbon atom form a cycloalkyl ring of four, five or six carbon atoms.

5 Claims, No Drawings

INSECTICIDAL ETHERS

This invention relates to novel insecticidal ethers, to processes and intermediates for their preparation, to insecticidal compositions comprising them and to methods of combating and controlling insect pests therewith.

In a first aspect the invention provides compounds of formula (I):

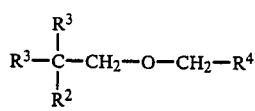

wherein $R^4$ represents a group selected from those groups represented by $R^5$ in insecticidally active compounds of formula:

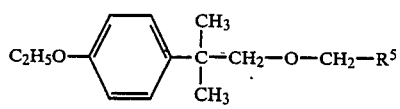

$R^3$ is selected from fluoromethyl and difluoromethyl, and either (a) $R^1$ and $R^2$ represent alkyl of one, two, three or four carbon atoms, or (b) $R^1$ and $R^2$ taken together with the adjacent carbon atom form a cycloalkyl ring of four, five or six carbon atoms.

Preferred compounds according to the invention are those according to formula (I) wherein $R^4$ represents a group of formula:

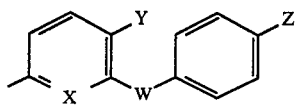

wherein W represents oxygen, the methylene group or nitrogen bearing a hydrogen atom, X represents nitrogen or carbon bearing a hydrogen atom and Y and Z are each selected from hydrogen and halogen. Particularly preferred compounds according to the invention are those according to formula (I) wherein $R^1$ and $R^2$ both represent methyl.

Examples of compounds according to the invention are given in Tables I and II. In Table I the compounds listed correspond to the formula (IA):

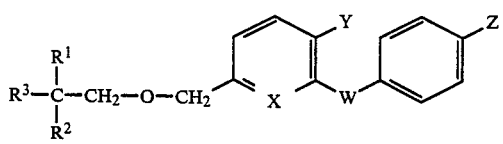

and in Table II the compounds listed correspond to the formula (IB):

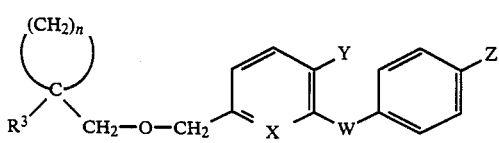

Values of $R^1$, $R^2$, $R^3$, n, X, Y, W and Z are given in the Tables.

TABLE I

| Compound No. | $R^1$ | $R^2$ | $R^3$ | W | X | Y | Z |
|---|---|---|---|---|---|---|---|
| 1 | CH₃ | CH₃ | CHF₂ | O | CH | F | H |
| 2 | CH₃ | CH₃ | CHF₂ | O | CH | H | H |
| 3 | CH₃ | C₂H₅ | CHF₂ | O | CH | H | H |
| 4 | CH₃ | CH₃ | CHF₂ | CH₂ | CH | F | H |
| 5 | CH₃ | CH₃ | CHF₂ | O | N | H | H |
| 6 | CH₃ | CH₃ | CHF₂ | NH | CH | F | H |
| 7 | CH₃ | CH₃ | CH₂F | O | CH | F | H |
| 8 | CH₃ | CH₃ | CH₂F | O | CH | H | H |
| 9 | CH₃ | C₂H₅ | CHF₂ | O | CH | F | H |
| 10 | CH₃ | C₂H₅ | CHF₂ | CH₂ | CH | F | H |
| 11 | CH₃ | C₂H₅ | CHF₂ | NH | CH | F | H |
| 12 | CH₃ | C₂H₅ | CHF₂ | O | N | H | H |
| 13 | CH₃ | CH₃ | CH₂F | CH₂ | CH | F | H |
| 14 | CH₃ | C₂H₅ | CH₂F | O | CH | H | H |
| 15 | CH₃ | C₂H₅ | CH₂F | O | CH | F | H |
| 16 | CH₃ | C₂H₅ | CH₂F | CH₂ | CH | F | H |
| 17 | CH₃ | CH₃ | CHF₂ | O | CH | F | Cl |
| 18 | CH₃ | CH₃ | CH₂F | O | CH | F | Cl |
| 19 | CH₃ | CH₃ | CHF₂ | O | CH | H | Cl |
| 20 | CH₃ | CH₃ | CH₂F | O | CH | H | Cl |

TABLE II

| Compound No. | n | $R^3$ | W | X | Y | Z |
|---|---|---|---|---|---|---|
| 21 | 4 | CHF₂ | O | CH | F | H |
| 22 | 4 | CHF₂ | O | CH | H | H |
| 23 | 4 | CHF₂ | CH₂ | CH | F | H |
| 24 | 4 | CH₂F | O | CH | H | H |
| 25 | 4 | CH₂F | O | CH | F | H |
| 26 | 4 | CH₂F | CH₂ | CH | F | H |
| 27 | 5 | CHF₂ | O | CH | H | H |
| 28 | 5 | CHF₂ | O | CH | F | H |
| 29 | 5 | CHF₂ | CH₂ | CH | F | H |
| 30 | 3 | CHF₂ | O | CH | H | H |
| 31 | 3 | CHF₂ | O | CH | F | H |
| 32 | 3 | CHF₂ | CH₂ | CH | F | H |
| 33 | 5 | CH₂F | O | CH | F | H |
| 34 | 3 | CH₂F | O | CH | F | H |
| 35 | 3 | CHF₂ | NH | CH | F | H |
| 36 | 3 | CH₂F | NH | CH | F | H |
| 37 | 3 | CHF₂ | O | CH | F | Cl |
| 38 | 4 | CHF₂ | O | CH | H | Cl |

Certain of the compounds according to formula (I) may contain at least one asymmetrically substituted carbon atom, for example in those compounds where the groups $R^1$ and $R^2$ are not identical. The scope of the invention includes all stereoisomeric forms of invention compounds arising from the presence of such asymmetric centres and mixtures of such isomers, including racemic mixtures.

The compounds of formula (I) wherein $R^3$ represents difluoromethyl may be prepared from the corresponding alcohols of formula (II):

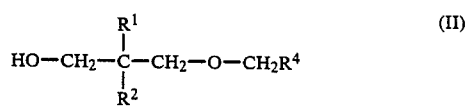

wherein $R^1$, $R^2$ and $R^4$ have any of the meanings given hereinabove, by oxidation to the corresponding aldehyde using, for example, pyridinium chlorochromate as described by Corey and Suggs in Tetrahedron Letters, 1975 page 2647, or the oxidation procedure described by Swern et al in the Journal of Organic Chemistry, 1978, vol 43, page 2482, followed by treatment of the aldehyde with an appropriate fluorinating agent, for example sulphur tetrafluoride or diethylamino-sulphur trifluoride. The compounds of formula (I) wherein $R^3$ represents fluoromethyl may also be prepared from the corresponding alcohols of formula (II) by conversion of the hydroxyl function to a displaceable derivative, such as the tosylate or mesylate derivative, followed by displacement by reaction with the fluoride anion, for example using potassium fluoride. The compounds of formula (II) may themselves be prepared by reaction of a 2,2-disubstituted-1,3-diol of formula (III):

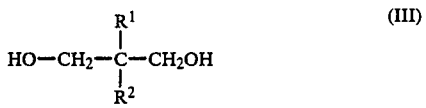

(III)

wherein $R^1$ and $R^2$ have any of the meanings given above, with a halide of formula $R^4CH_2$-Hal, wherein Hal represents a halogen atom, preferably bromine or chlorine and $R^4$ has any of the meanings given above, the reaction preferably taking place in the presence of a base. Those diols of formula (III) wherein $R^2$ and $R^3$ together with the adjacent carbon atom form a cycloalkyl ring may b prepared from a dialkyl ester of the appropriate cyclo-alkyl-1,1-dicarboxylic acid by reduction, for example using lithium aluminium hydride.

The general synthetic routes described above may not be appropriate for the preparation of compounds of formula (IA) and (IB) wherein W represents nitrogen bearing a hydrogen atom because of the possibility of competing reactions at the amino group. An alternative synthetic route suitable for the preparation of 1,1-difluoro-2,2-dimethyl-3-(3-phenylamino-4-fluorobenzyloxy)propane is illustrated, by way of example, in Scheme I. Further details of the processes described above are given in the Examples hereinafter.

Scheme I

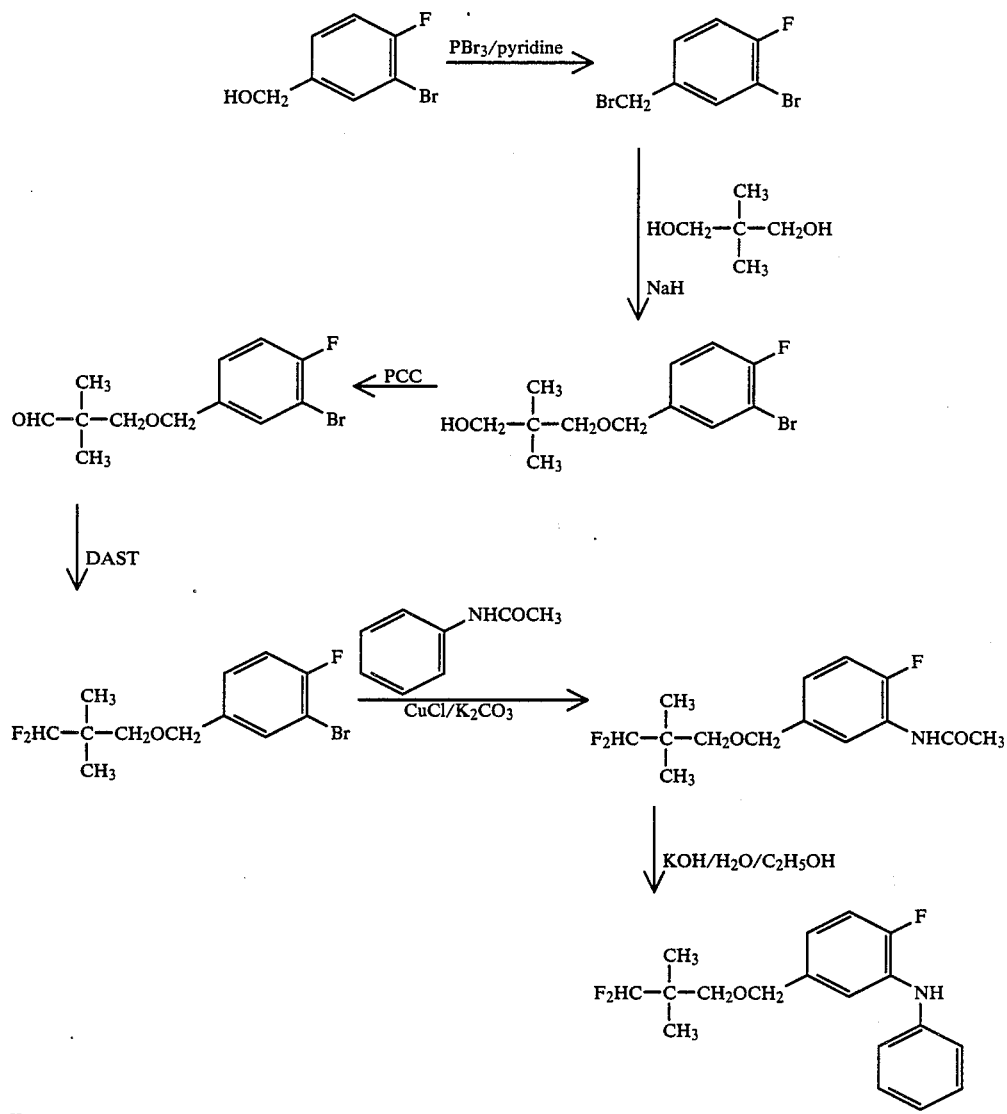

Key:
PCC = Pyridinium chlorochromate
DAST = Diethylaminosulphur trifluoride

The compounds of formula I may be used to combat and control infestations of insect pests and also other invertebrate pests, for example, acarine pests. The insect and acarine pests which may be combated and controlled by the use of the invention compounds include those pests associated with agriculture (which term includes the growing of crops for food and fibre products, horticulture and animal husbandry), forestry, the storage of products of vegetable origin, such as fruit, grain and timber, and also those pests associated with the transmission of diseases of man and animals.

In order to apply the compounds to the locus of the pests they are usually formulated into compositions which include in addition to the insecticidally active ingredient or ingredients of formula (I) suitable inert diluent or carrier materials, and/or surface active agents.

The compounds of the invention may be the sole active ingredient of the composition or they may be admixed with one or more additional active ingredients such as insecticides, insecticide synergists, herbicides, fungicides or plant growth regulators where appropriate.

Suitable additional active ingredients for inclusion in admixture with the compounds of the invention may be compounds which will broaden the spectrum of activity of the compounds of the invention or increase their persistence at the locus of the pest. They may synergise the activity of the compounds of the invention or complement the activity for example by increasing the speed of effect, improving knockdown or overcoming repellency. Additionally multi-component mixtures of this type may help to overcome or prevent the development of resistance to individual components.

The particular insecticide, herbicide or fungicide included in the mixture will depend upon its intended utility and the type of complementar action required.

Examples of suitable insecticides include the following:
(a) Pyrethroids such as permethrin, esfenvalerate, deltamethrin, cyhalothrin, biphenthrin, fenpropathrin, cyfluthrin, tefluthrin, fish safe pyrethroids for example ethofenprox, natural pyrethrin, tetramethrin, s-bioallethrin, fenfluthrin, prallethrin and 5-benzyl-3-furylmethyl-(E)-(1R,3S)-2,2-dimethyl-3-(2-oxothiolan-3-ylidenemethyl)cyclopropane carboxylate;
(b) Organophosphates such as profenofos, sulprofos, methyl parathion, azinphos-methyl, demeton-s-methyl, heptenophos, thiometon, fenamiphos, monocrotophos, profenophos, triazophos, methamidophos, dimethoate, phosphamidon, malathion, chlorpyrifos, phosalone, fensulfothion, fonofos, phorate, phoxim, pyrimiphosmethyl, fenitrothion or diazinon;
(c) Carbamates (including aryl carbamates) such as pirimicarb, cloethocarb, carbofuran, ethiofencarb, aldicarb, thiofurox, carbosulfan, bendiocarb, fenobucarb, propoxur or oxamyl;
(d) Benzoyl ureas such as triflumuron, chlorofluazuron;
(e) Organic tin compounds such as cyhexatin, fenbutatin oxide, azocyclotin;
(f) Macrolides such as avermectins or milbemycins, for example such as abamectin, avermectin, and milbemycin;
(g) Hormones such as juvenile hormone, juvabione, or ecdysones;
(h) Pheromones;
(i) Organochlorine compounds such as benzene hexachloride, DDT, chlordane, endosulfan or dieldrin.

In addition to the major chemical classes of insecticide listed above, other insecticides having particular targets may be employed in the mixture if appropriate for the intended utility of the mixture. For instance selective insecticides for particular crops, for example stemborer specific insecticides for use in rice such as cartap or buprofezin, can be employed. Alternatively insecticides specific for particular insect species/stages for example ovolarvicides such as clofentezine, flubenzimine, hexythiazox and tetradifon, motilicides such as dicofol or propargite, acaricides such as bromopropylate, chlorobenzilate, or insect growth regulators such as hydramethylon, cyromazin, methoprene, chlorofluazuron and diflubenzuron may also be included in the compositions.

Examples of suitable insecticide synergists for use in the compositions include piperonyl butoxide, sesamex, and dodecyl imidazole.

Suitable herbicides, fungicides and plant growth regulators for inclusion in the compositions will depend upon the intended target and the effect required. An example of a rice selective herbicide which can be included is propanil, an example of a plant growth regulator for use in cotton is "Pix", and examples of fungicides for use in rice include blasticides such as blasticidin-S. The choice of other ingredients to be used in mixture with the active ingredient will often be within the normal skill of the formulator, and will be made from known alternatives depending upon the total effect to be achieved.

The ratio of the compound of the invention to any other active ingredient in the composition will depend upon a number of factors including the type of insect pests to be controlled, and the effects required from the mixture. However in general, the additional active ingredient of the composition will be applied at about the rate it would usually be employed if used on its own, or at a lower rate if synergism occurs.

The compositions may be in the form of dusting powders wherein the active ingredient is mixed with a solid diluent or carrier, for example kaolin, bentonite, kieselguhr, or talc, or they may be in the form of granules, wherein the active ingredient is absorbed in a porous granular material, for example pumice.

Alternatively the compositions may be in the form of liquid preparations to be used as aerosols, dips or sprays. Dips and sprays are generally aqueous dispersions or emulsions of the active ingredient in the presence of one or more known wetting agents, dispersing agents or emulsifying agents (surface active agents. Aerosol compositions may contain the active ingredient or ingredients, a propellant and an inert diluent, for example odourless kerosene or alkylated benzenes.

Wetting agents, dispersing agents and emulsifying agents may be of the cationic, anionic or non-ionic type. Suitable agents of the cationic type include, for example, quaternary ammonium compounds, for example cetyltrimethyl ammonium bromide. Suitable agents of the anionic type include, for example, soaps, salts of aliphatic monoesters or sulphuric acid, for example sodium lauryl sulphate, salts of sulphonated aromatic compounds, for example sodium dodecylbenzenesulphonate, sodium, calcium or ammonium lignosulphonate, or butylnaphthalene sulphonate, and a mixture of the sodium salts of diisopropyl- and triisopropylnaphtalene sulphonates. Suitable agents of the non-ionic type include, for example, the condensation products of ethylene oxide with fatty alcohols such as oleyl alcohol or cetyl alcohol, or with alkyl phenols such as octyl phenol, nonyl phenol and octyl cresol. Other non-ionic agents are the partial esters derived from long chain fatty acids and hxxitol anhydrides, the condensation products of the said partial esters with ethylene oxide, and the lecithins.

The compositions may be prepared by dissolving the active ingredient in a suitable solvent, for example, a ketonic solvent such as diacetone alcohol, or an aromatic solvent such as trimethylbenzene and adding the mixture so obtained to water which may contain one or more known wetting, dispersing or emulsifying agents.

Other suitable organic solvents are dimethyl formamide, ethylene dichloride, isopropyl alcohol, propylene glycol and other glycols, diacetone alcohol, toluene, kerosene, white oil, methylnaphthalene, xylenes and trichloroethylene, N-methyl-2-pyrrolidone and tetrahydrofurfuryl alcohol (THFA).

The compositions which are to be used in the form of aqueous dispersions or emulsions are generally supplied in the form of a concentrate containing a high proportion of the active ingredient or ingredients, the said concentrate to be diluted with water before use. These concentrates are often required to withstand storage for prolonged periods and after such storage, to be capable of dilution with water to form aqueous preparations which remain homogenous for a sufficient time to enable them to be applied by conventional spray equipment. The concentrates may contain 10–85% by weight of the active ingredient or ingredients. When diluted to form aqueous preparations such preparations may contain varying amounts of the active ingredient depending upon the purpose for which they are to be used. For agricultural or horticultural purposes, an aqueous preparation containing between 0.0001% and 0.1% by weight of the active ingredient is particularly useful.

In use the compositions are applied to the pests, to the locus of the pests, to the habitat of the pests, or to growing plants liable to infestation by the pests, by any of the known means of applying pesticidal compositions, for example, by dusting or spraying.

The compositions of the invention are very toxic to wide varieties of insect and other invertebrate pests, including, for example, the following:
*Myzus persicae* (aphids)
*Aphis fabae* (aphids)
*Megoura viceae* (aphids)
*Aedes aegypti* (mosquitos)
Anopheles spp. (mosquitos)
Culex spp. (mosquitos)
*Dysdercus fasciatus* (capsids)
*Musca domestica* (houseflies)
*Pieris brassicae* (white butterfly, larvae)
*Plutella maculipennis* (diamond back moth, larvae)
*Phaedon cochleariae* (mustard beetle)
Aonidiella spp. (scale insects)
Trialeuroides spp. (white flies)
*Blattella germanica* (cockroaches)
*Blatta orientalis* (cockroaches)
*Periplaneta americana* (cockroaches)
*Spodoptera littoralis* (cotton leaf worm)
*Heliothis virescens* (tobacco budworms)
*Chortiocetes terminifera* (locusts)
Diabrotica spp. (rootworms)
*Nilaparvata lugens* (plant hoppers)
Agrotis spp. (cutworms)
*Chilo suppressalis* (rice stem borer)
*Chilo partellus* (maize stem borers)
*Nephotettix cincticeps* (leaf hoppers)
*Tetranychus urticae* (red spider mite)
*Tetranychus cinnabarinus* (carmine spider mite)
*Panonychus ulmi*
*Panonychus citri*

In addition to providing effective control of lepidopteran pests of cotton, for example Spodoptera spp. and Heliothis spp, the compounds of formula (I) and compositions comprising them have also been shown to be particularly useful in the control of pests of maize and rice such as Chilo spp. (stem borers), Nilaparvata spp. and Nephotettix spp. (plant and leaf hoppers). Some of the compounds show high levels of activity against rice pests at rates which are not toxic to fish, thus enabling their use in paddy rice where fish are cultivated in the paddy.

The compounds of formula (I) and compositions comprising them may also be useful in combating insect and acarine pests which infest domestic animals, such as *Lucilia sericata*, and ixodid ticks such as Boophilus spp., Ixodes spp., Amblyomma spp., Rhipicephalus spp; and Dermaceutor spp. They are effective in combating both susceptible and resistant strains of these pests in their adult, larval and intermediate stages of growth, and may be applied to the infested host animal by topical, oral or parenteral administration.

The following Examples illustrate various aspects of this invention. In the preparation Examples the products were usually identified and characterised by means of nuclear magnetic reasonance spectroscopy and infrared spectroscopy. In each case where a product is specifically named its spectral characteristics are consistent with the assigned structure. Except where stated otherwise, exemplified compounds having one or more asymmetrically substituted carbon atoms were prepared in racemic form.

In the Examples, Gas Liquid Chromatography (GLC) retention times were determined on a Hewlett Packard 5890 Gas Chromatograph, using a Chrompak, CPSil 5CB column of 12.5 m length and 0.2 mm internal diameter. Unless otherwise stated, the injection temperature was 100° C., and a temperature gradient of 15° C./minute employed, up to a maximum temperature of 280° C., maintained for 4 minutes. The carrier gas was helium at a column head pressure maintained at 11 psi. Alternative injection and maximum temperature are indicated in the Examples where appropriate.

$^1$H Nuclear Magnetic Resonance (NMR) spectrometry was performed at a frequency of 270 MHz on a Jeol FX 270 NMR spectrometer, unless otherwise indicated. 90 MHz, 60 MHz and 400 MHz $^1$H NMR spectrometry were performed using Jeol FX 90 Q, Jeol PMX60 SI and Jeol GX400 spectrometers respectively. $^{19}$F NMR spectrometry was performed on a Jeol FX90Q spectrometer at a frequency of 84.26 MHz. All NMR shift values ($\delta$) are quoted in ppm relative to a standard (TMS or CFCl$_3$.)

Molecular Ion (M$^+$) peaks (measured in atomic mass units) were determined on one of three mass spectrometers: Jeol DX303, Kratos MS80 or Hewlett Packard HP 5992.

EXAMPLE 1

This Example illustrates the preparation of 2,2-dimethyl-3-(4-fluoro-3-phenoxybenzyloxy)propan-1-ol.

A solution of 2,2-dimethylpropan-1,3-diol (5.2 g) in tetrahydrofuran (35 cm$^3$) was added in small aliquots to a stirred suspension of sodium hydride (0.6 g) in tetrahydrofuran (35 cm³) with cooling. After effervescence had ceased tetrabutylammonium iodide (1.7 g) was added to the resultant grey suspension followed by addition of a solution of 4-fluoro-3-phenoxybenzyl bromide (7.1 g) in dry tetrahydrofuran (30 cm³) at the ambient temperature (ca. 25° C.), and the mixture stirred for a further 2 hours. The mixture was poured into water and the products extracted into ethyl acetate. The organic extracts were combined, dried over anhydrous magnesium sulphate and concentrated by evaporation of the solvent; the residual oil was identified as a mixture of 2,2-dimethyl-3-(4-fluoro-3-phenoxybenzyloxy)propan-1-ol and some unreacted 2,2-dimethylpropan-1,3-diol by nmr and infra red spectroscopic examination.

$^1$H NMR (CDCl$_3$): 0.9 (s,6H); 2.2 (broad s, 1H); 3.3 (s,2H); 3.5 (s,2H); 4.4 (s,2H); 6.9–7.4 (m,8H)

Infra red (liquid film): 3400, 1595, 1515, 1280, 1215 cm$^{-1}$ (major peaks only).

EXAMPLE 2

The following compounds were prepared from the appropraate diol and benzylbromide using the method described in Example 1.

(i) 2,2-Dimethyl-3-(3-phenoxybenzyloxy)propan-1-ol (obtained as a mixture containing the title compound and a small amount of unreacted 2,2-dimethylpropan-1,3-diol)

$^1$H NMR (CDCl$_3$): 0.9 (s,6H); 2.4 (broad s, 1H); 3.3 (s,2H); 3.5 (broad d, 2H); 4.5 (s,2H); and 6.8–7.5 (m,9H)

IR (liquid film): 3340, 1585, 1490 and 1255 cm$^{-1}$.

(ii) (RS)-2-Ethyl-2-methyl-3-(3-phenoxybenzyloxy)propan-1-ol

In this case the crude oil was distilled in a Kugelrohr apparatus, the title compound boiling at 200° C. (0.03 mmHg).

$^1$H NMR (CDCl$_3$): 0.8 (m,6H); 1.4 (m,2H;; 2.5 (broad s,1H); 3.4 (s,2H); 3.5 (broad s, 2H); 4.5 (s,2H); and 6.9–7.5 (m,9H) .

IR (liquid film): 3450, 1590, 1490, 1260, 1220, and 695 cm$^{-1}$ (major peaks only).

(iii) 2,2-Dimethyl-3-(4-fluoro-3-benzylbenzyloxy)propan-1-ol

IR (liquid film): 3700–3000 cm$^{-1}$ (OH)

GLC retention time: 8.22 minutes (78% pure)

(iv) 1-Hydroxymethyl-1-(4-fluoro-3-phenoxybenzyloxymethyl)cyclopentane.

The preparation of 1,1-bis-(hydroxymethyl)cyclopentane is described in Example 11.

$^1$H NMR (CDCl$_3$): 1.2–1.65 (8H,m); 2.55 (1H, broad t); 3.38 (2H,s); 3.49 (2H,d); 4.43 (2H,s); 7.0–7.4 (8H,m)

IR (liquid film): 3430 cm$^{-1}$ (OH)

EXAMPLE 3

This Example illustrates the stages in the preparation of 2,2-dimethyl-3-[(6-phenoxypyrid-2-yl)methyloxy)-propan-1-ol.

(i) 2-Chloromethyl-6-phenoxypyridine

Triethylamine (2.27 cm³) was added portionwise to a stirred solution of 2-hydroxymethyl-6-phenoxypyridine (3 g), para-toluenesulphonyl chloride (3.7 g), and 4-dimethylaminopyridine (1.17 g) in dichloromethane (30 cm³), whilst the reaction mixture was maintained at the ambient temperature (ca. 22° C.) under an atmosphere of nitrogen. After a period of four hours, the reaction mixture was poured into diethyl ether, and washed sequentially with saturated aqueous sodium bicarbonate, water and brine. The organic layer was then dried, and after removal of the solvent by evaporation under reduced pressure, the crude product was subjected to column chromatography on silica gel using dichloromethane as eluent to give 2-chloromethyl-6-phenoxypyridine (2.05 g).

$^1$H NMR (CDCl$_3$): 4.55 (s,2H); 6.75 (d,1H); 7.2 (m,4H); 7.4 (m,2H); 7.7 (t,1H)

IR (liquid film): 2980, 1595, 1575, and 1445 cm$^{-1}$.

GLC retention time: 4.27 minutes.

(ii) 2,2-Dimethyl-3-[(6-phenoxypyrid-2-yl)methyloxy]-propan-1-ol.

2,2-Dimethylpropan-1,3-diol was reacted with 2-chloromethyl-6-phenoxypyridine according to the procedure set out in Example 1, using dimethylformamide as solvent.

The crude product was purified by column chromatography on silica gel using petroleum ether (boiling range 40°–60° C.) containing 40% by volume diethyl ether as eluent, to give 2,2-dimethyl-3-[(6-phenoxypyrid-2-yl)-methyloxy]propan-1-ol as a red oil.

$^1$H NMR (CDCl$_3$): 0.95 (s,6H); 2.8 (broad s, 1lH); 3.4 (s,2H); 3.5 (s,2H); 4.5 (s,2H); 6.65 (d,1H); 7.15 (m,4H); 7.4 (t,2H); 7.65 (t,1H)

IR (liquid film): 3400, 2960, 2870, 1598, 1580 and 1440 cm$^{-1}$

GLC retention time: 7.29 minutes

EXAMPLE 4

This Example illustrates the preparation of 2,2-dimethyl-3-(4-fluoro-3-phenoxybenzyloxy)propan-1-al.

A solution of 2,2-dimethyl-3-(4-fluoro-3-phenoxybenzyloxy)propan-1-ol (5.0 g) in dichloromethane (30 cm³) was added dropwise to a stirred suspension of pyridinium chlorochromate (6.77 g) in dichloromethane (20 cm³) whilst the reaction temperature was maintained within the range 0°–5° C. When the addition was complete the mixture was allowed to warm to the ambient temperature over a period of 2 hours. The solvent was removed and the residual oil (3.0 g) purified by column chromatography using a silica gel support and eluting with petroleum ether (boiling range 40°–60° C.) containing 10% by volume diethyl ether to yield 2,2-dimethyl-3-(4-fluoro-3-phenoxybenzyloxy)propan-1-al (1.5 g) as a yellow oil.

$^1$H NMR (CDCl$_3$): 1.1 (s,6H); 3.5 (s,2H); 4.5 (s,2H); 7.0–7.5 (m,8SH); 9.6 (s,1H)

IR (liquid film): 1735, 1590, 1510, 1490, 1280, 1210 cm$^{-1}$ (major peaks only).

EXAMPLE 5

The following aldehydes were prepared by oxidation of the appropriate alcohol using the method of Example 4.

(i) 2,2-Dimethyl-3-(3-phenoxybenzyloxy)propan-1-al $^1$H NMR (CDCl$_3$): 1.1 (s,6H; 3.45 (s,2H); 4.5 (s,2H); 6.8–7.4 (m,9H); and 9.55 (s,1H)

IR (liquid film): 1735, 1590, 1490, 1445, 1250, 1215, 1100 and 690 cm$^{-1}$ (ii) (RS)-2-Ethyl-2-methyl-3-(3-phenoxybenzyloxy)propan-1-al In this case the crude oil was purified by distillation in a Kugelrohr oven, the title compound boiling at 170° C. (0.07 mmHg).

$^1$H NMR (CDCl$_3$): 0.8 (t,3H); 1.05 (s,3H); 1.55 (m,2H); 3.4 (d,1H); 3.5 (d,1H); 4.45 (s,2H); 6.9–7.4 (m,9H); and 9.5 (s,1H)

IR (liquid film): 1730, 1590, 1490, 1260, 1220, and 695 cm$^{-1}$ (iii) 2,2-Dimethyl-3-(4-fluoro-3-benzylbenzyloxy)propan-1-al
$^1$H NMR (CDCl$_3$): 1.05 (s,6H); 3.39 (s,2H); 3.99 (s,2H); 4.40 (s,2H); 6.95–7.35 (m,8H); 9.52 (s,1H)
IR (liquid film): 2880, 1732, 1608, 1508, 1250, and 1105 cm$^{-1}$ (iv) 2,2-Dimethyl-3-[(6-phenoxypyrid-2-yl)methyloxy]propan-1-al
$^1$H NMR (CDCl$_3$): 1.1 (s,6H); 3.55 (s,2H); 4.5 (s,2H); 6.7 (d,1H); 7.0–7.2 (m,4H); 7.4 (t,2H); 7.65 (t,1H); 9.6 (s,1H)
IR (liquid film): 2980, 2880, 1730, 1598, 1580 and 1440 cm$^{-1}$
GLC retention time: 6.91 minutes.

(v) 1-Formyl-1-(4-fluoro-3-phenoxybenzyloxymethyl)cyclopentane
$^1$H NMR (CDCl$_3$): 1.4–1.65 (8H,m); 3.44 (2H,s); 4.4 (2H,s); 6.8–7.4 (8H,m); 9.4 (1H,s)
IR (liquid film): 1727 cm$^{-1}$ (C=O)

EXAMPLE 6

This Example illustrates the stages in the preparation of 1-fluoro-2,2-dimethyl-3-(4-fluoro-3-phenoxybenzyloxy)propane

Stage 1:
2,2-Dimethyl-3-(4-fluoro-3-phenoxybenzyloxy)prop-1-yl p-toluenesulphonate A mixture of 2,2-dimethyl-3-(4-fluoro-3-phenoxybenzyloxy)propan-1-ol (5 g), p-toluenesulphonyl chloride (3.75 g) and pyridine (10 cm$^3$) was stirred at the ambient temperature (ca. 20° C.) for 24 hours. The mixture was poured into dilute aqueous hydrochloric acid solution and hhe aqueous mixture extracted with ethyl acetate (3×250 cm$^3$). The combined organic layers were washed with brine, then dried over anhydrous magnesium sulphate. Evaporation of the solvent under reduced pressure gave a dark oil (4 g) which was purified by column chromatography on a silica gel support, eluting with petroleum ether (boiling range (60°–80° C.) containing 20% by volume ethyl acetate, to give the title compound (3.9 g) as a yellow oil.
GLC retention time: 13.78 minutes

Stage 2:
1-Fluoro-2,2-dimethyl-3-(4-fluoro-3-phenoxybenzyloxy)propane

A mixture of 2,2-dimethyl-3-(4-fluoro-3-phenoxybenzyloxy)propy-1-yl p-toluenesulphonate (2.5 g), potassium fluoride (0.8 g) and tetraethylene glycol (7 cm$^3$) was heated at 160° C. (under a drying tube to exclude moisture) for 3 hours. The reaction mixture was allowed to cool and stood at the ambient temperature for 17 hours. The mixture was poured into water and the products extracted into diethyl ether (2×200 cm$^3$). The combined organic extracts were washed with water and dried over anhydrous magnesium sulphate. Evaporation of the solvent under reduced pressure gave an orange oil (1.5 g) which was passed through a short silica gel column using petroleum ether (boiling range 40°–60° C.) containing 10% by volume diethyl as eluent. Analysis of the resulting oil indicated 3 major components which were separated and isolated by high pressure liquid chromatography (eluting with hexane containing 1% by volume ethyl acetate). The first and third fractions were identified as 1-chloro-2,2-dimethyl-3-(4-fluoro-3-phenoxybenzyloxy)propane (0.25 g—thought to have been formed owing to the presence of chloride ion contamination of the starting materials) and 2-(4-fluoro-3-phenoxybenzyloxy)-but-1-ene (an elimination by-product) respectively. The title compound (0.29 g) was obtained as the second eluted fraction; characterising data for this compound are given below:
$^1$H NMR (CDCl$_3$): 0.92 (6H,s); 3.22 (2H,s); 4.18 (2H,d); 4.43 (2H,s); 6.8–7.4 (8H,m)
Molecular ion: 306

EXAMPLE 7

This Example illustrates the stages in the preparation of 1-fluoro-2,2-dimethyl-3-(phenoxybenzyloxy)propane

Stage 1: 2,2-Dimethyl-3-(phenoxybenzyloxy)prop-1-yl methanesulphonate

N,N-Dimethylaminopyridine (0.015 g) was added to a stirred solution of methanesulphonyl chloride (0.2 g) in pyridine (0.3 cm$^3$) and the mixture was cooled to 0° C.; a solution of 2,2-dimethyl-3-(3-phenoxybenzyloxy)propan-1-ol (0.25 g) in pyridine (0.1 cm$^3$) was added to cooled mixture. The cooling bath was removed and the stirred mixture was allowed to warm to the ambient temperature (ca 20° C.). Stirring was continued for 3 hours and the mixture was then allowed to stand for 2 days. The mixture was partitioned between ethyl acetate (50 cm$^3$) and water (50 cm$^3$) and the organic phase separated. The aqueous layer was extracted with further ethyl acetate and the combined organic layers were washed with water and brine, and dried over anhydrous magnesium sulphate. Evaporation of the solvent under reduced pressure gave an orange oil containing the title compound and residual methanesulphonyl chloride, which was partially removed by evaporation at reduced pressure. The crude material (0.26 g) was used without further purification.
60 MHz $^1$H NMR (CDCl$_3$): 1.0 (6H,s); 2.9 (3H,s); 3.2 (2H,s); 3.62 (3H,s - trace of methanesulphonyl chloride); 4.0 (2H,s) 4.44 (2H,s); 6.8–7.4 (9H,m).
GLC retention time: 10.51 minutes

Stage 2:
1-fluoro-2,2-dimethyl-3-(3-phenoxybenzyloxy)propane

This compound was prepared from 2,2-dimethyl-3-(3-phenoxybenzyloxy)prop-1-yl methanesulphonate using the method described for Stage 2 of Example 6.
Purification of the crude reaction products by high pressure liquid chromatography gave three separated products, identified as 1-chloro-2,2-dimethyl-3-(3-phenoxybenzyloxy)propane (first fraction), 2(3-phenoxybenzyloxy)but-l-ene (third fraction) and the title compound, for which characterising data are given below:
$^1$H NMR (CDCl$_3$): 0.9 (6H,s); 3.22 (2H,s); 4.2 (2H,d); 4.44 (2H,s); 6.8–7.4 (9H,m)
Molecular ion: 288

EXAMPLE 8

This Example illustrates the preparation of 1,1-difluoro-2,2-dimethyl-3-(4-fluoro-3-phenoxybenzyloxy)propane.

A stirred solution of 2,2-dimethyl-3-(4-fluoro-3-phenoxybenzyloxy)propan-1-al (0.5 g) in trichlorofluoromethane (3 cm$^3$) was cooled to 0° C. under an atmosphere of nitrogen. Diethylaminosulphur trifluoride (0.8 g) was added dropwise to the cooled solution and a slight exotherm was observed. The stirred mixture was allowed to warm to the ambient temperature (ca. 20° C.) and stirred for a further one hour. The mixture was partitioned between diethyl ether and water (effervescence and exotherm noted), the organic layer was separated and the aqueous layer extracted twice with diethyl ether. The combined organic layers were washed with water and dried over anhydrous magnesium sulphate. Evaporation of the solvent under reduced pressure gave a yellow oil which was purified by column chromatography on a silica gel support, eluting with petroleum ether (boiling range 40°-60° C.) containing 2% by volume diethyl ether, to give the title compound (0.23 g) as an oil.

$^1$H NMR (CDCl$_3$): 1.0 (6H,s); 3.25 (2H,s); 4.4 (2H,s); 5.7 (1H,t); 6.9-7.4 (8H,m)

GLC retention time: 6.23 minutes

EXAMPLE 9

The following compounds were prepared from the appropriate aldehydes using the method described in Example 8.

(i) 1,1-Difluoro-2,2-dimethyl-3-(3-phenoxybenzyloxy)propane

In this case the reaction was carried out at −78° C.

$^1$H NMR (CDCl$_3$): 1.0 (6H,s); 3.3 (2H,s); 4.46 (2H,s); 5.7 (1H,t); 6.8-7.5 (9H,m)

$^{19}$F NMR (CDCl$_3$): −132.587 (d) Plus small signal at −111.481 (d) due to impurity GLC retention time: 6.91 minutes (ii) (RS)-1,1-Difluoro-2-ethyl-2-methyl-3(3-phenoxybenzyloxy)propane In this case the reaction was carried out at −20° C.

$^1$H NMR (CDCl$_3$): 0.85 (3H,t); 0.91 (3H,s); 1.50 (2H,m); 3.31 (2H,s); 4.45 (2H,s); 5.74 (1H,t); 6.9-7.4 (9H,m)

$^{19}$F NMR (CDCl$_3$): −32.399 (dd, J=57 Hz)

GLC retention time: 7.48 minutes (iii) 1,1-Difluoro-2,2-dimethyl-3-(4-fluoro-3-benzylbenzyloxy)propane In this case the reaction was initially carried out at −78° C., but little product was detected. Further diethylaminosulphur trifluoride was added at the ambient temperature and the reaction mixture was stood for 17 hours then stirred for 5 hours. Analysis by GLC showed the reaction to be almost complete at this stage and the product was isolated.

$^1$H NMR (CDCl$_3$): 1.0 (6H,s); 3.24 (2H,s); 4.0 (2H,s); 4.39 (2H,s); 5.64 (1H,t); 7.26 (8H,m)

$^{19}$F NMR (CDCl$_3$): −132.58 (2F,d); −120.1 (1F,s)

GLC retention time: 6.87 minutes (iv) 1-Difluoromethyl-1-(4-fluoro-3-phenoxybenzyloxymethyl)cyclopentane In this case the reaction was carried out at −78° C.

$^1$H NMR (CDCl$_3$): 1.2-1.9 (8H,m); 3.31 (2H,s); 4.41 (2H,s); 5.9 (1H,t); 7.0-7.4 (8H,m)

19F NMR (CDCl$_3$): −130.334 (2F,d); −133.040 (1F,s)

GLC retention time: 8.54 minutes (v) 1,1-Difluoro-2,2-dimethyl-3-[(6-phenoxypyrid-2-yl)methyloxy]propane $^1$H NMR (CDCl$_3$): 1.03 (6H,s); 3.3 (2H,s); 4.50 (2H,s); 5.75 (1H,t); 6.65 (1H,d); 7.15 (4H,m); 7.4 (2H,t); 7.65 (1H,t)

$^{19}$F NMR (CDCl$_3$): −132.4 (d)

GLC retention time: 6.71 minutes

EXAMPLE 10

This Example illustrates the stages in the preparation of 1,1-difluoro-2,3-dimethyl-3-(4-fluoro-3-phenylaminobenzyloxy)propane.

Stage 1: 4-fluoro-3-bromobenzaldehyde

Powdered aluminium trichloride (226 g) was suspended in dry dichloromethane (250 cm$^3$) and the suspension was cooled to 0° C. 4-Fluorobenzaldehyde (124 g) was added to the stirred suspension, the temperature of the mixture being maintained below 10° C. during the addition. Stirring of the dark reaction mixture was continued at 0° C. for 15 minutes and bromine (176g) was then added in a single addition. The mixture was then heated at the reflux temperature for a total of 14 hours, the mixture being stood overnight at the ambient temperature twice within this heating period. At this point, analysis by GLC suggested only 78% bromination. Further bromine (5 cm$^3$) was added and heating at the reflux temperature continued for a further 2 hours, but little change was observed on GLC analysis. The mixture was cooled to the ambient temperature and poured into ice (1 kg). After the ice had melted, the aqueous layer was separated and extracted with dichloromethane. The combined organic layers were washed with sodium metabisulphite solution, to remove unreacted bromine, and brine and then dried over anhydrous magnesium sulphate. Evaporation of the solvent under reduced pressure gave a red oil which was purified by distillation using a 15 cm Vigreux column. The title compound (84 g) was collected as the major fraction, boiling at 144° C./28 mmHg.

$^1$H NMR (CDCl$_3$): 7.2-8.3 (3H,m); 9.94 (1H,s)

IR (liquid film): 1711 cm$^{-1}$ (C=O)

GLC retention time: 3.88 minutes (50°-250° C. run)

Stage 2: 3-Bromo-4-fluorobenzyl alcohol

Lithium aluminium hydride (0.075 g) was added to a stirred solution of 3-bromo-4-fluorobenzaldehyde (1.2 g) in dry tetrahydrofuran (20 cm$^3$), the temperature being maintained below 5° C. by external cooling. The temperature of the reaction mixture was then allowed to rise to the ambient value (ca 20° C.) and the mixture was stirred for 2 hours; GLC analysis of a withdrawn sample indicated 82% conversion at this time, and further lithium aluminium hydride (0.025 g) was therefore added to the mixture. After a further 1.5 hours GLC analysis indicated that the reaction was complete. The mixture aas poured into water (20 cm$^3$) and the products extracted into diethyl ether (3×20 cm$^3$). The combined ethereal extracts were washed with brine and dried over anhydrous magnesium sulphate. Evaporation of the solvent under reduced pressure gave the title compound in high purity.

$^1$H NMR (CDCl$_3$): 1.78 (1H,t); 4.65 (2H,d); 7.1-7.7 (3H,m)

IR (liquid film): 3347 cm$^{-1}$ (OH, broad)

GLC retention time: 2.34 minutes

Stage 3: 3-Bromo-4-fluorobenzyl bromide

Pyridine (0.7 cm$^3$) and a solution of 3-bromo-4-fluorobenzyl alcohol (5 g) in dry toluene (50 cm$^3$) were added to a stirred solution of phosphorus tribromide (2.64 g) in dry toluene (50 cm$^3$) under an atmosphere of nitrogen, the temperature of the reaction mixture being maintained at −10° C. during the addition. The mixture was allowed to warm to the ambient temperature (ca. 20° C.) and was stirred for one hour. The mixture was poured into ice and the products extracted into diethyl ether. The combined organic extracts were washed with brine and dried over anhydrous magnesium sulphate to give an orange-red oil, shown by thin layer chromatography to contain two components. NMR spectroscopy of the mixture suggested the presence of a phosphite intermediate and the required product. The oil was redissolved in dry toluene (50 cm³) and further phosphorus tribromide (0.2 g) and pyridine (0.7 cm³) added. The mixture was stirred at 50° C. for 4 hours and then stood at the ambient temperature for 17 hours. The mixture was poured into ice and sodium bicarbonate solution added to neutralise the resulting acid mixture. The products were extracted into diethyl ether, and the combined organic extracts washed with brine and dried over anhydrous magnesium sulphate. Evaporation of the solvent gave a white solid which was purified by flash column chromatography on a silica gel support, eluting with petroleum ether containing 5% by volume diethyl ether, to give the title compound (4.6 g) as a colourless crystalline solid.

90 MHz $^1$H NMR (CDCl$_3$): 4.42 (2H,s); 7.0–7.7 (3H,m)

Molecular ion: 266

Stage 4:
2,2-Dimethyl-3-(3-bromo-4-fluorobenzyloxy)propan-1-ol

This compound was prepared from 3-bromo-4-fluorobenzyl bromide and 2,2-dimethylpropan-1,3-diol using the method of Example 1.

GLC retention time: 5.32 minutes
IR (liquid film): 3417 cm$^{-1}$ (OH, broad)

Stage 5:
2,2-Dimethyl-3-(3-bromo-4-fluorobenzyloxy)propan-1-al

This compound was prepared from 2,2-dimethyl-3-(3-bromo-4-fluorobenzyloxy)propan-1-ol using the method of Example 4.

$^1$H NMR (CDCl$_3$): 1.03 (6H,s); 3.38 (2H,s); 4.37 (2H,s); 6.9–7.5 (3H,m); 9.49 (1H,s)
GLC retention time: 4.87 minutes
IR (liquid film): 1728 cm$^{-1}$ (C=O)

Stage 6:
1,1-Difluoro-2,2-dimethyl-3-(3-bromo-4-fluorobenzyloxy)propane

Diethylmminosulphur trifluoride (3.34 g) was added to 2,2-dimethyl-3-(3-bromo-4-fluorobenzyloxy)propan-1-al under an atmosphere of nitrogen, the temperature of the mixture being maintained below −28° C. during the addition (note that stirring was inhibited by the reaction mixture solidifying at this temperature). The mixture was allowed to warm to the ambient temperature and stirring continued for one hour. The mixture was dissolved in diethyl ether (100 cm³) and water was cautiously added to destroy excess diethylaminosulphur trifluoride; a vigorous reaction and exotherm were observed and hydrofluoric acid was released. The mixture was separated and the aqueous layer extracted with diethyl ether. The combined organic layers were washed with sodium bicarbonate solution and brine, then dried over anhydrous magnesium sulphate. Evaporation of the solvent under reduced pressure gave an orange oil (ca. 2 g) which was purified by column chromatography on a silica gel support, eluting with petroleum ether, to give the title compound (0.75 g)

$^1$H NMR (CDCl$_3$): 1.0(6H,s); 3.3 (2H,s); 4.42 (2H,s); 5.76 (1H,t); 6.8–7.7 (3H,m)
GLC retention time: 3.91 minutes
Molecular ion: 310

Stage 7:
1,1-Difluoro-2,2-dimethyl-3-[3-(N-phenyl-N-acetylamino)-4-fluorobenzyloxy]propane A mixture of 1,1-difluoro-2,2-dimethyl-3-(3-bromo-4-fluorobenzyloxy)propane (1.5 g), acetanilide (0.716 g), cuprous chloride (0.1 g); potassium carbonate (0.67 g), dry N,N-dimethylformamide (10 cm³) and tri[2-(2-methoxyethoxy)ethyl]amine (catalytic quantity) was heated at 158° C. for 4 days under an atmosphere of nitrogen; the mixture was then stood at the ambient temperature for 1 week. The combined organic extracts were washed with water and brine and dried over anhydrous magnesium sulphate. Evaporation of the solvent under reduced pressure gave a dark oil which was subjected to flash column chromatography on a silica gel support, eluting firstly with petroleum ether (boiling range 40°–6° C.) containing 2% by volume ethyl acetate (to give starting materials and a small amount of the deacylated product) and secondly with petroleum ether (boiling range 40°–60° C.) containing 50% by volume ethyl acetate, to give the title compound as a dark oil (0.68 g).

90 MHz$^1$H NMR (CDCl$_3$): 1.0 (6H,s); 2.08 (3H,s); 3.23 (2H,s); 4.4 (2H,s); 5.65 (1H,t); 7.0–7.4 (8H,m)
IR (liquid film): 1684 cm$^{-1}$ (C=O)
Molecular ion: 365

Stage 8:
1,1-Difluoro-2,2-dimethyl-3-(3-phenylamino-4-fluorobenzyloxy)propane 1,1-Difluoro-2,2-dimethyl-3-[3-(N-phenyl-N-acetylamino)-4fluorobenzyloxy]propane (0.5 g) was suspended in a 1 molar solution of potassium hydroxide in water containing 20% by volume ethanol and the mixture was heated at the reflux temperature for 8 hours. After standing overnight at the ambient temperature, the mixture was shaken several times with ethyl acetate and the combined organic extracts washed with water and brine, and dried over anhydrous magnesium sulphate. Evaporation of the solvent under reduced pressure gave a brown oil which was purified by column chromatography on a silica gel supoort, eluting with petroleum ether (boiling range 40°–60° C.) containing 10% by volume ethyl acetate, to give the title compound (0.23 g) as a pale yellow oil.

$^1$H NMR (CDCl$_3$): 0.99 (6H,s); 1.6 (s, trace of water); 3.28 S (2H,s); 4.39 (2H,s); 5.72 (1H,t); 5.8 (broad s, 1H); 6.8–7.4 (8H,m)
IR (liquid film): 3429 cm$^{-1}$ (NH)
GLC retention time: 7.72 minutes
Molecular ion: 323

EXAMPLE 11

This Example illustrates the stages in the preparation of 1,1-bis-(hydroxymethyl)cyclopentane.

Stage 1: Diethyl cyclopentane-1,1-dicarboxylate

A solution of sodium ethoxide in ethanol was prepared by cautiously dissolving sodium (7.19 g) in ethanol (100 cm³). The stirred solution was cooled in an ice bath and to it was added dropwise a solution of diethyl malonate (20 g) in ethanol (20 cm³); a thick yellow suspension was formed. The mixture was stirred for a further 15 minutes and 1,4-dibromobutane (27 g) was added. The mixture was allowed to warm to the ambient temperature and stirred for 17 hours. The mixture was then partitioned between diethyl ether and water and the aqueous layer separated and extracted three further times with diethyl ether. The combined organic layers were dried over anhydrous magnesium sulphate and the solvent evaporated under reduced pressure to leave the title compound (23.3 g) as a dark oil. The product was used without further purification in Stage 2.

Stage 2: 1,1-bis(hydroxymethyl)cyclopentane

A solution of diethyl cyclopentane-1,1-dicarboxylate (23.3 g) in dry tetrahydrofuran (50 cm$^3$) was added to a stirred suspension of lithium aluminium hydride (2.3 g) in dry tetrahydrofuran (150 cm$^3$) at 0° C. under an atmosphere of nitrogen. The mixture was allowed to warm to the ambient temperature then stood for 17 hours; GLC analysis of a withdrawn sample indicated the presence of starting ester at this time. Two further portions of lithium aluminium hydride (0.5 g and 3.0 g) were added and the mixture stirred for a total of 2.5 hours. After this time GLC analysis showed no starting material. The mixture was poured into a mixture of diethyl ether and water. The aqueous layer was separated and extracted twice with diethyl ether. The combined organic layers were washed with brine and dried over anhydrous magnesium sulphate. Evaporation of the solvent under reduced pressure gave the title compound (12.95 g) in 89% purity (by GLC analysis) as an off-white solid.

60 MHz $^1$H NMR (CDCl$_3$): 0.9–1.7 (8H,m); 3.4 (2H, broad s); 3.5 (4H,s)

GLC retention time: 1.54 minutes

EXAMPLE 12

The activity of the Product was determined using variety of insect pests. The Product was used in the form of liquid preparations containing 500, 100 or 10 parts per million (ppm) by weight of the Product. The preparations were made by dissolving the Product in acetone and diluting the solutions with water containing b 0.01% by weight of a wetting agent sold under the trade name "LISSAPOL" NX until the liquid preparations contained the required concentration of the Product. "Lissapol" is a Registered Trade Mark.

The test procedure adopted with regard to each pest was basically the same and comprised supporting a number of the pests on a medium which was usually a host plant or a foodstuff on which the pests feed, and treating either or both the pests and the medium with the preparations. The mortality of the pests was then assessed at perods usually varying from one to three days after the treatment.

In the case of the species *Musca domestica* (housefly), additional tests to determine the knockdown effect of the compounds were performed. Details are given in Table III.

The results of the tests are given in Table IV for each of the Products, at the rate in parts per million given in the second column, as a grading of mortality designated as A, B or C wherein A indicates 80–100% mortality or knockdown, B indicates 50–79% mortality or knockdown and C indicates less than 50% mortality or knockdown.

In Table IV the pest organism used is designated by a letter code and the pest species, the support medium or food, and the type and duration of test is given in Table III.

TABLE III

| CODE LETTERS (Table IV) | TEST SPECIES | SUPPORT MEDIUM/FOOD | TYPE OF TEST | DURATION (days) |
|---|---|---|---|---|
| TU | *Tetranychus urticae* (spider mites - adult) | French bean leaf | Contact | 3 |
| MP | *Myzus persicae* (aphids) | Chinese Cabbage leaf | Contact | 3 |
| NC | *Nephotettix cincticeps* (green leaf hopper - nymphs) | Rice plant | Contact | 3 |
| NL | *Niloparvata lugens* (brown plant hopper - nymphs) | Rice plant | Contact | 3 |
| HV | *Heliothis virescens* (tobacco budworm - larvae) | Cotton leaf | Residual | 3 |
| DB | *Diabrotica balteata* (rootworm larvae) | Filter paper/ maize seed | Residual | 3 |
| BG | *Blattella germanica* (cockroach nymphs) | Plastic pot | Residual | 3 |
| MD | *Musca domestica* (houseflies - adults) | Cotton wool/ sugar | Contact | 1 |
| MD/KD | *Musca domestica* (houseflies - adults) | Cotton/wool sugar | Knockdown | 4 hours |
| SP | *Spodoptera exigua* (lesser army worm - larvae) | Cotton leaf | Residual | 3 |

"Contact" test indicates that both pests and medium were treated and "residual" indicates that the medium was treated before infestation with the pests.

This Example illustrates the insecticidal properties of the Products of this invention.

TABLE IV

| Compound No. | Rate (ppm) | TU | MP | NC | NL | HV | DB | BG | MD | MD/KD | SP |
|---|---|---|---|---|---|---|---|---|---|---|---|
| 1 | 500 | C | C | — | A | A | A | A | A | A | A |
| 2 | 500 | C | C | A | — | C | A | A | A | A | C |
| 3 | 500 | C | C | C | — | C | A | C | B | B | A |
| 4 | 500 | C | C | — | — | C | A | B | A | C | B |
| 5 | 500 | A | B | — | A | C | A | A | A | A | A |
| 6 | 500 | A | A | A | — | A | A | — | C | B | A |

TABLE IV-continued

| Compound No. | Rate (ppm) | TU | MP | NC | NL | HV | DB | BG | MD | MD/KD | SP |
|---|---|---|---|---|---|---|---|---|---|---|---|
| 7 | 500 | C | C | A | — | A | A | A | A | A | A |
| 8 | 500 | C | C | A | — | B | A | C | B | C | A |
| 21 | 500 | C | C | A | — | B | A | — | C | C | C |

I claim:

1. A compound of formula (I):

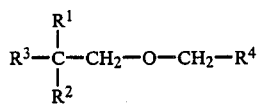

wherein $R^4$ represents a group of the formula:

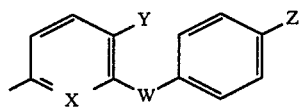

wherein W represents oxygen, the methylene group or nitrogen bearing a hydrogen atom, X represents nitrogen or carbon bearing a hydrogen atom and Y and Z are each selected from hydrogen and halogen $R^3$ is selected from fluoromethyl and difluoromethyl, and either (a) $R^1$ and $R^2$ represent alkyl of one, two, three or four carbon atoms, or (b) $R^1$ and $R^2$ taken together with the adjacent carbon atom form a cycloalkyl ring of four, five or six carbon atoms.

2. A compound according to claim 1 wherein $R^1$ and $R^2$ both represent methyl.

3. A compound selected from the group consisting of 1,1-difluoro-2,2-dimethyl-3-(4-fluoro-3-phenoxybenzyloxy)propane,
1,1-difluoro-2,2-dimethyl-3-(3-phenoxybenzyloxy)propane,
1,1-difluoro-2,2-dimethyl-3-(4-fluoro-3-benzylbenzyloxy)propane,
1,1-difluoro-2,2-dimethyl-3-[(6-phenoxypyrid-2-yl)methyloxy]propane,
1,1-difluoro-2,2-dimethyl-3-(3-phenylamino-4-fluorobenzyloxy)propane,
1-fluoro-2,2-dimethyl-3-(4-fluoro-3-phenoxybenzyloxy))propane,
1-fluoro-2,2-dimethyl-3-(3-phenoxybenzyloxy)propane.

4. An insecticidal composition comprising an insecticidally effective amount of a compound according to claim 1 in association with an insecticidally inert diluent or carrier material.

5. A method of combating insect pests at a locus which comprises treating the locus with an insecticidally effective amount of the composition of claim 4.

* * * * *